United States Patent
Craft

(10) Patent No.: US 9,102,989 B2
(45) Date of Patent: Aug. 11, 2015

(54) NON-REVERTIBLE β-OXIDATION BLOCKED CANDIDA TROPICALIS

(75) Inventor: David L. Craft, Ft. Thomas, KY (US)

(73) Assignee: Cognis IP Management GmbH, Duesseldorf (DE)

( * ) Notice: Subject to any disclaimer, the term of this patent is extended or adjusted under 35 U.S.C. 154(b) by 865 days.

(21) Appl. No.: 12/244,677

(22) Filed: Oct. 2, 2008

(65) Prior Publication Data

US 2010/0167361 A1 Jul. 1, 2010

Related U.S. Application Data

(63) Continuation of application No. 10/444,467, filed on May 22, 2003, now abandoned.

(60) Provisional application No. 60/383,332, filed on May 23, 2002.

(51) Int. Cl.
| | | |
|---|---|---|
| *C12N 1/19* | (2006.01) | |
| *C12R 1/74* | (2006.01) | |
| *C12P 7/44* | (2006.01) | |

(52) U.S. Cl.
CPC .... *C12R 1/74* (2013.01); *C12P 7/44* (2013.01)

(58) Field of Classification Search
CPC .............. C12R 1/72; C12R 1/74; C12N 1/16; C12N 15/81; C12N 15/1079; C12P 7/44
See application file for complete search history.

(56) References Cited

U.S. PATENT DOCUMENTS

| | | | |
|---|---|---|---|
| 5,254,466 A | 10/1993 | Picataggio et al. | |
| 5,620,878 A | 4/1997 | Picataggio et al. | |
| 5,648,247 A | 7/1997 | Picataggio et al. | |
| 6,288,275 B1 | 9/2001 | Turner | |
| 6,331,420 B1 | 12/2001 | Wilson et al. | |
| 6,673,613 B2 | 1/2004 | Craft et al. | |
| 6,790,640 B2 | 9/2004 | Craft et al. | |
| 7,049,112 B2 | 5/2006 | Wilson et al. | |
| 7,063,972 B2 | 6/2006 | Wilson et al. | |
| 7,109,009 B2 | 9/2006 | Wilson et al. | |
| 7,160,708 B2 | 1/2007 | Eirich et al. | |
| 7,388,084 B2 | 6/2008 | Wilson et al. | |
| 2003/0119145 A1* | 6/2003 | Donnelly | 435/69.1 |
| 2004/0265980 A1* | 12/2004 | Zhang et al. | 435/134 |

FOREIGN PATENT DOCUMENTS

EP WO00/20566 4/2000

OTHER PUBLICATIONS

Rothstein, RJ. One-step gene disruption in yeast. Methods Enzymol. 1983;101:202-11.*
H.J. Rehm and G. Reed (eds.), Aliphatic Hydrocarbons in Biotechnology, vol. 169, Verlag chewie, Weinheim (1984).
F.M. Ausubel, et al. (eds.) Current Protocols in Molecular Biology, Supplement 5, 13.7.1 (1989).
Toshiro Furukawa, Toru Matsuyoshi, and Shoichi Kise, Selection of High Brassylic Acid Producing Strains of Torulopsis candida by Single-Cell Cloning and by Mutation, J. Ferment Technol., vol. 64, No. 2, 97-101 (1986).
Zhou Jianlong and Chiao Juishen, The Regulation of Alanine on the Fermentation of Long-Chain Dicarboxylic Acids in *Candida tropicalis* NPcoN22, p. 4, (1988) (English Abstract Only).
Brachmann, Carrie Baker, et al.—Designer Deletion Strains Derived from *Saccharomyces cerevisiae* S288C: a Useful set of Strains and Plasmids for PCR-mediated Gene Disruption and Other Applications, Yeast vol. 14: 115-132 (1998).
De Backer, M. et al., Genomic Profiling of the Response of *Candida albicans* to Itraconazole Treatment Using a DNA Microarray, Antimicrobial Agents and Chemotherapy, 45:1660 (2001).
Ogino, S. et al., Studies of Utilization of Hydrocarbons by Yeasts, Part II. Diterminal Oxidation of Alkanes by Yeast, Agr. Biol. Chem., vol. 29, No. 11, pp. 1009-1015 (1965).
Shiio, I. et al., Microbial Production of Long-chain Dicarboxylic Acids from n-Alkanes, Part I. Screening and Properties of Microorganisms Producing Dicarboxylic Acids, Agr. Biol. Chem., vol. 35, No. 13, pp. 2033-2042 (1971).
Vamecq, Joseph and Draye, Jean-Pierre, Interactions between the ω- and β-Oxidations of Fatty Acids, J. Biochem. 102, 225-234 (1987).
Ueda, Mitsuyoshi, et al. Peroxisomal Localization of Enzymes Related to Fatty Acid β-Oxidation in an n-Alkane-grown Yeast, Candida tropicalis, Agric. Biol. Chem., 49 (6), 1821-1828, 1985.
Okino, Hiroshi, et al. Production of Macrocyclic Musk Compounds via Alkanedioic Acids Produced from n-Alkanes; B.M. Lawrence, B.D. Mookherjee and B.J. Willis (Editors), Flavors and Fragrances: A World Perspective. Proceedings of the 10th International Congress of Essential Oils, Fragrances and Flavors, Washington, DC, U.S.A., Nov. 16-20, 1986.
Sambrook, et al, Molecular Cloning: A Laboratory Manual, 2ed. Cold spring Harbor Press, USA (1989).
Okino, et al. Production of Macrocyclic Musk Compounds via Alkanedioic Acids Produced from N-Alkanes, B.M. Lawrence, et al. (eds) Flavors and Fragrances: A World Perspective; Proceedings of the 10th International Congress of Essential Oils, Fragrances and Flavors, Washington, DC, U.S.A., Nov. 16-20, 1986, 1988 Elsevier Science Publishers B.V., Amsterdam, pp. 753-760.
Jef D. Boeke, Francois LaCroute and Gerald R. Fink, A Positive Selection for Mutants Lacking Orotidine-5'-phosphate Decarboxylase Activity in Yeast: 5-Fluoro-orotic Acid Resistance, Mol Gen Genet (1984) 197:345-346.
F.F. Hill, I. Venn, and K.L. Lukas, Studies on the Formation of Long-Chain Dicarboxylic Acids from Pure n-alkanes by a Mutant of *Candida tropicalis*, Appl Microbiol Biotechnol (1986) 24: 168-174.
Eva Kärgel, et al., Candida maltosa NADPH-cytochrome P450 Reductase: Cloning of a Full-length cDNA, Heterologous Expression in *Saccharomyces cerevisiae* and Function of the N-terminal Region for Membrane Anchoring and Proliferation of the Endoplasmic Reticulum, Yeast, vol. 12: 333-348 (1996).
Glenwyn D. Kemp, F. Mark Dickinson, and Colin Ratledge, Inducible Long Chain Alcohol Oxidase from Alkane-Grown *Candida tropicalis*, Appl Microbiol Biotechnol (1988) 29:370-374.

(Continued)

*Primary Examiner* — Michele K Joike
(74) *Attorney, Agent, or Firm* — Servilla Whitney LLC

(57) ABSTRACT

Genetically modified strains of *C. tropicalis*, which will not revert to wild-type activity at the POX 4 and/or POX 5 locus, are disclosed. The strains are β-oxidation blocked and have been transformed through homologous recombination with a construct which deletes a portion of the POX 4 and/or POX 5 gene. The modified strains may be used to increase yields of dicarboxylic acids produced in host cells of the strains. Methods for blocking the β-oxidation pathway in a *C. tropicalis* host cell are also provided.

6 Claims, 6 Drawing Sheets

(56) References Cited

OTHER PUBLICATIONS

Branko Kozulić, Klaus Mosbach and Franz Meussdoerffer, Biosynthesis of Soluble Carnitine Acetyltransferases from the Yeast *Candida tropicalis*, Biochem, J. (1988) 253, 845-849.

David R. Nelson, et al., P450 Superfamily: Update on New Sequences, Gene Mapping, Accession Numbers and Nomenclature, Pharmacogenetics (1996) 6, 1-42.

Moriya Ohkuma, et al., CYP52 (cytochrome P450alk) Multigene Family in Candida maltosa: Identification and Characterization of Eight Members, DNA and Cell Biology, vol. 14, No. 2, (1995), pp. 163-173.

Rehm, H.J., and I. Reiff. 1981. Mechanisms and occurrence of microbial oxidation of long-chain alkanes, p. 175-215. In A. Fiechter (ed.), Advances in biochemical engineering, vol. 19. Springer-Verlag, Berlin, Germany.

Dominique Sanglard and John C. Loper, Characterization of the alkane-inducible cytochrome P450 (P450alk) Gene from the Yeast *Candida tropicalis*: Identification of a New P450 Gene Family, Gene, 76 (1989) 121-136.

Wolfgang Seghezzi, et al., Identification and Characterization of Additional Members of the Cytochrome P450 Multigene Family CYP52 of *Candida tropicalis*, DNA and Cell Biology, vol. 11, No. 10, 1992, pp. 767-780.

Michele Gilewicz, et al., Hydroxylase Regulation in *Candida tropicalis* Grown on Alkanes, Can. J. Microbiol (1979) 25:201-206.

Kaiser, et al., eds., Methods in Yeast Genetics, 1994 Edition, Cold Spring Harbor Laboratory Press.

\* cited by examiner

FIG. 1

POX 4 Sequence

```
          10         20         30         40         50         60         70         80
GAGCTCCAATTGTAATATTTCGGGAGAAATATCGTTGGGGTAAAACAACAGAGAGAGAGAGGGAGAGATGGTTCTGGTAG 90        100        110        120        130        140        150        160
AATTATAATCTGGTTGTTGCAAATGCTACTGATCGACTCTGGCAATGTCTGTAGCTCGCTAGTTGTATGCAACTTAGGTG 170        180        190        200        210        220        230        240
TTATGCATACACACGGTTATTCGGTTGAATTGTGGAGTAAAAATTGTCTGAGTTGTGTCTTAGCTACTGGCTGGCCCCCC 250        260        270        280        290        300        310        320
GCGAAAGATAATCAAAATTACACTTGTGAATTTTTGCACACACACCGATTAACATTTCCCTTTTTTGTCCACCGATACAC 330        340        350        360        370        380        390        400
GCTTGCCTCTTCTTTTTTTTCTCTGTGCTTCCCCCTCCTGTGACTTTTTCCACCATTGATATAAAATCAACTCCATTTCC 410        420        430        440        450        460        470        480
CTAAAATCTCCCCAGATTCTAAAAACAACTTCTTCTCTTCTGCTTTTCCTTTTTTTTTGTTATATTTATTTACCATCCCT 490        500        510        520        530          540            550
TTTTTTTGAATAGTTATTCCCCACTAACATTGTTCAAATCTTCACGACATA ATG ACT TTT ACA AAG AAA AAC
                                                     M   T   F   T   K   K   N>

560                 570                 580                 590                 600             610
GTT AGT GTA TCA CAA GGT CCT GAC CCT AGA TCA TCC ATC CAA AAG GAA AGA GAC AGC TCC
 V   S   V   S   Q   G   P   D   P   R   S   S   I   Q   K   E   R   D   S   S>

620                 630                 640                 650                 660             670
AAA TGG AAC CCT CAA CAA ATG AAC TAC TTC TTG GAA GGC TCC GTC GAA AGA AGT GAG TTG
 K   W   N   P   Q   Q   M   N   Y   F   L   E   G   S   V   E   R   S   E   L>

680                 690                 700                 710                 720             730
ATG AAG GCT TTG GCC CAA CAA ATG GAA AGA GAC CCA ATC TTG TTC ACA GAC GGC TCC TAC
 M   K   A   L   A   Q   Q   M   E   R   D   P   I   L   F   T   D   G   S   Y>

740                 750                 760                 770                 780             790
TAC GAC TTG ACC AAG GAC CAA CAA AGA GAA TTG ACC GCC GTC AAG ATC AAC AGA ATC GCC
 Y   D   L   T   K   D   Q   Q   R   E   L   T   A   V   K   I   N   R   I   A>

800                 810                 820                 830                 840             850
AGA TAC AGA GAA CAA GAA TCC ATC GAC ACT TTC AAC AAG AGA TTG TCC TTG ATT GGT ATC
 R   Y   R   E   Q   E   S   I   D   T   F   N   K   R   L   S   L   I   G   I>

860                 870                 880                 890                 900             910
TTT GAC CCA CAG GTC GGT ACC AGA ATT GGT GTC AAC CTC GGT TTG TTC CTT TCT TGT ATC
 F   D   P   Q   V   G   T   R   I   G   V   N   L   G   L   F   L   S   C   I>

920                 930                 940                 950                 960             970
AGA GGT AAC GGT ACC ACT TCC CAA TTG AAC TAC TGG GCT AAC GAA AAG GAA ACC GCT GAC
 R   G   N   G   T   T   S   Q   L   N   Y   W   A   N   E   K   E   T   A   D>

980                 990                1000                1010                1020            1030
GTT AAA GGT ATC TAC GGT TGT TTC GGT ATG ACC GAA TTG GCC CAC GGT TCC AAC GTT GCT
 V   K   G   I   Y   G   C   F   G   M   T   E   L   A   H   G   S   N   V   A>

1040                1050                1060                1070                1080            1090
GGT TTG GAA ACC ACC GCC ACA TTT GAC AAG GAA TCT GAC GAG TTT GTC ATC AAC ACC CCA
 G   L   E   T   T   A   T   F   D   K   E   S   D   E   F   V   I   N   T   P>

1100                1110                1120                1130                1140            1150
CAC ATT GGT GCC ACC AAG TGG TGG ATT GGT GGT GCT GCT CAC TCC GCC ACC CAC TGT TCT
 H   I   G   A   T   K   W   W   I   G   G   A   A   H   S   A   T   H   C   S>
```

FIG. 1 (cont'd.)

```
        1160           1170           1180           1190           1200           1210
GTC TAC GCC AGA TTG ATT GTT GAC GGT CAA GAT TAC GGT GTC AAG ACT TTT GTT GTC CCA
 V   Y   A   R   L   I   V   D   G   Q   D   Y   G   V   K   T   F   V   V   P>

1220           1230           1240           1250           1260           1270
TTG AGA GAC TCC AAC CAC GAC CTC ATG CCA GGT GTC ACT GTT GGT GAC ATT GGT GCC AAG
 L   R   D   S   N   H   D   L   M   P   G   V   T   V   G   D   I   G   A   K>

1280           1290           1300           1310           1320           1330
ATG GGT AGA GAT GGT ATC GAT AAC GGT TGG ATC CAA TTC TCC AAC GTC AGA ATC CCA AGA
 M   G   R   D   G   I   D   N   G   W   I   Q   F   S   N   V   R   I   P   R>

1340           1350           1360           1370           1380           1390
TTC TTT ATG TTG CAA AAG TTC TGT AAG GTT TCT GCT GAA GGT GAA GTC ACC TTG CCA CCT
 F   F   M   L   Q   K   F   C   K   V   S   A   E   G   E   V   T   L   P   P>

1400           1410           1420           1430           1440           1450
TTG GAA CAA TTG TCT TAC TCC GCC TTG TTG GGT GGT AGA GTC ATG ATG GTT TTG GAC TCC
 L   E   Q   L   S   Y   S   A   L   L   G   G   R   V   M   M   V   L   D   S>

1460           1470           1480           1490           1500           1510
TAC AGA ATG TTG GCT AGA ATG TCC ACC ATT GCC TTG AGA TAC GCC ATT GGT AGA AGA CAA
 Y   R   M   L   A   R   M   S   T   I   A   L   R   Y   A   I   G   R   R   Q>

1520           1530           1540           1550           1560           1570
TTC AAG GGT GAC AAT GTC GAT CCA AAA GAT CCA AAC GCT TTG GAA ACC CAA TTG ATA GAT
 F   K   G   D   N   V   D   P   K   D   P   N   A   L   E   T   Q   L   I   D>

1580           1590           1600           1610           1620           1630
TAC CCA TTG CAC CAA AAG AGA TTG TTC CCA TAC TTG GCT GCT GCC TAC GTC ATC TCC GCT
 Y   P   L   H   Q   K   R   L   F   P   Y   L   A   A   A   Y   V   I   S   A>

1640           1650           1660           1670           1680           1690
GGT GCC CTC AAG GTT GAA GAC ACC ATC CAT AAC ACC TTG GCT GAA TTG GAC GCT GCC GTT
 G   A   L   K   V   E   D   T   I   H   N   T   L   A   E   L   D   A   A   V>

1700           1710           1720           1730           1740           1750
GAA AAG AAC GAC ACC AAG GCT ATC TTT AAG TCT ATT GAC GAC ATG AAG TCA TTG TTT GTT
 E   K   N   D   T   K   A   I   F   K   S   I   D   D   M   K   S   L   F   V>

1760           1770           1780           1790           1800           1810
GAC TCT GGT TCC TTG AAG TCC ACT GCC ACT TGG TTG GGT GCT GAA GCC ATT GAC CAA TGT
 D   S   G   S   L   K   S   T   A   T   W   L   G   A   E   A   I   D   Q   C>

1820           1830           1840           1850           1860           1870
AGA CAA GCC TGT GGT GGT CAC GGT TAC TCG TCC TAC AAC GGC TTC GGT AAA GCC TAC AAC
 R   Q   A   C   G   G   H   G   Y   S   S   Y   N   G   F   G   K   A   Y   N>

1880           1890           1900           1910           1920           1930
GAT TGG GTT GTC CAA TGT ACT TGG GAA GGT GAC AAC AAT GTC TTG GCC ATG AGT GTT GGT
 D   W   V   V   Q   C   T   W   E   G   D   N   N   V   L   A   M   S   V   G>

1940           1950           1960           1970           1980           1990
AAG CCA ATT GTC AAG CAA GTT ATC AGC ATT GAA GAT GCC GGC AAG ACC GTC AGA GGT TCC
 K   P   I   V   K   Q   V   I   S   I   E   D   A   G   K   T   V   R   G   S>

2000           2010           2020           2030           2040           2050
ACC GCT TTC TTG AAC CAA TTG AAG GAC TAC ACT GGT TCC AAC AGC TCC AAG GTT GTT TTG
 T   A   F   L   N   Q   L   K   D   Y   T   G   S   N   S   S   K   V   V   L>

2060           2070           2080           2090           2100           2110
AAC ACT GTT GCT GAC TTG GAC GAC ATC AAG ACT GTC ATC AAG GCT ATT GAA GTT GCC ATC
 N   T   V   A   D   L   D   D   I   K   T   V   I   K   A   I   E   V   A   I>

2120           2130           2140           2150           2160           2170
ATC AGA TTG TCC CAA GAA GCT GCT TCT ATT GTC AAG AAG GAA TCT TTC GAC TAT GTC GGC
 I   R   L   S   Q   E   A   A   S   I   V   K   K   E   S   F   D   Y   V   G>
```

FIG. 1 (cont'd.)

```
     2180         2190         2200         2210         2220         2230
GCT GAA TTG GTT CAA CTC TCC AAG TTG AAG GCT CAC CAC TAC TTG TTG ACT GAA TAC ATC
 A   E   L   V   Q   L   S   K   L   K   A   H   H   Y   L   L   T   E   Y   I>

2240         2250         2260         2270         2280         2290
AGA AGA ATT GAC ACC TTT GAC CAA AAG GAC TTG GTT CCA TAC TTG ATC ACC CTC GGT AAG
 R   R   I   D   T   F   D   Q   K   D   L   V   P   Y   L   I   T   L   G   K>

2300         2310         2320         2330         2340         2350
TTG TAC GCT GCC ACT ATT GTC TTG GAC AGA TTT GCC GGT GTC TTC TTG ACT TTC AAC GTT
 L   Y   A   A   T   I   V   L   D   R   F   A   G   V   F   L   T   F   N   V>

2360         2370         2380         2390         2400         2410
GCC TCC ACC GAA GCC ATC ACT GCT TTG GCC TCT GTG CAA ATT CCA AAG TTG TGT GCT GAA
 A   S   T   E   A   I   T   A   L   A   S   V   Q   I   P   K   L   C   A   E>

2420         2430         2440         2450         2460         2470
GTC AGA CCA AAC GTT GTT GCT TAC ACC GAC TCC TTC CAA CAA TCC GAC ATG ATT GTC AAT
 V   R   P   N   V   V   A   Y   T   D   S   F   Q   Q   S   D   M   I   V   N>

2480         2490         2500         2510         2520         2530
TCT GCT ATT GGT AGA TAC GAT GGT GAC ATC TAT GAG AAC TAC TTT GAC TTG GTC AAG TTG
 S   A   I   G   R   Y   D   G   D   I   Y   E   N   Y   F   D   L   V   K   L>

2540         2550         2560         2570         2580         2590
CAG AAC CCA CCA TCC AAG ACC AAG GCT CCT TAC TCT GAT GCT TTG GAA GCC ATG TTG AAC
 Q   N   P   P   S   K   T   K   A   P   Y   S   D   A   L   E   A   M   L   N>

2600         2610         2620         2630         2640         2650
AGA CCA ACC TTG GAC GAA AGA GAA AGA TTT GAA AAG TCT GAT GAA ACC GCT GCT ATC TTG
 R   P   T   L   D   E   R   E   R   F   E   K   S   D   E   T   A   A   I   L>

2660         2670         2680         2690         2700         2710         2720
TCC AAG TAA GAATAGAAGAGAGTGACTCTTTTGATAAGAGTCGCAAATTTGATTTCATAAGTATATAT
 S   K   *>

2730        2740        2750        2760        2770        2780        2790        2800
TCATTATGTAAAGTAGTAAATGGAAAATTCATTAAAAAAAAAGCAAATTTCCGTTGTATGCATACTCCGAACACAAAACT 2810        2820        2830        2840
AGCCCCGGAAAAACCCTTAGTTGATAGTTGCGAATTTAGGTCGAC
```

```
Sequence Range:   1 to 1712

10         20         30         40         50         60         70         80
GGTACCGAGC TCACGAGTTT TGGGATTTTC GAGTTTGGAT TGTTTCCTTT GTTGATTGAA TTGACGAAAC CAGAGGTTTT 90        100        110        120        130        140        150        160
CAAGACAGAT AAGATTGGGT TTATCAAAAC GCAGTTTGAA ATATTCCAGT TGGTTTCCAA GATATCTTGA AGAAGATTGA 170        180        190        200        210        220        230        240
CGATTTGAAA TTTGAAGAAG TGGAGAAGAT CTGGTTTGGA TTGTTGGAGA ATTTCAAGAA TCTCAAGATT TACTCTAACG 250        260        270        280        290        300        310        320
ACGGGTACAA CGAGAATTGT ATTGAATTGA TCAAGAACAT GATCTTGGTG TTACAGAACA TCAAGTTCTT GGACCAGACT 330        340        350        360        370        380        390        400
GAGAATGCCA CAGATATACA AGGCGTCATG TGATAAAATG GATGAGATTT ATCCCACAAT TGAAGAAAGA GTTTATGGAA 410        420        430        440        450        460        470        480
AGTGGTCAAC CAGAAGCTAA ACAGGAAGAA GCAAACGAAG AGGTGAAACA AGAAGAAGAA GGTAAATAAG TATTTTGTAT 490        500        510        520        530        540        550        560
TATATAACAA ACAAAGTAAG GAATACAGAT TTATACAATA AATTGCCATA CTAGTCACGT GAGATATCTC ATCCATTCCC 570        580        590        600        610        620        630        640
CAACTCCCAA GAAAAAAAAA AAGTGAAAAA AAAAATCAAA CCCAAAGATC AACCTCCCCA TCATCATCGT CATCAAACCC
```

FIG. 2

```
       650          660          670          680          690          700          710          720
CCAGCTCAAT TCGCAATGGT TAGCACAAAA ACATACACAG AAAGGGCATC AGCACACCCC TCCAAGGTTG CCCAACGTTT
            M  V   S   I   K   T   Y   T   E   R   A   S   A   H   P   S   K   V   A   Q   R   L>

730          740          750          760          770          780          790          800
ATTCCGCTTA ATGGAGTCCA AAAAGACCAA CCTCTGCGCC TCGATCGACG TGACCACAAC CGCCCGAGTTC CTTTCGCTCA
 F  R   L   M   E   S   K   K   T   N   L   C   A   S   I   D   V   T   T   T   A   E   F   L   S   L>

810          820          830          840          850          860          870          880
TCGACAAGCT CGGTCCCCAC ATCTGTCTCG TGAAGACGCA CATCGATATC ATCTCAGACT TCAGCTACGA GGGCACGATT
 I  D   K   L   G   P   H   I   C   L   V   K   T   H   I   D   I   I   S   D   F   S   Y   E   G   T   I>

890          900          910          920          930          940          950          960
GAGCCGGTTGC TTGTGCTTGC AGAGCGCCAC GGGTTCTTGA TATTCGAGGA CAGGAAGTTT GCTGATATCG GAAACACCGT
 E  P   L   L   V   L   A   E   R   H   G   F   L   I   F   E   D   R   K   F   A   D   I   G   N   T   V>

970          980          990         1000         1010         1020         1030         1040
GATGTTGCAG TACACCTCCG GGGTATACCG GATCGCGGCG TGGAGTGACA GCACGGAGTG ACTGGGAAGG
 M  L   Q   Y   T   S   G   V   Y   R   I   A   A   W   S   D   I   T   N   A   H   G   V   T   G   K>

1050         1060         1070         1080         1090         1100         1110         1120
GCGTCGTTGA AGGGTTGAAA CGCGGGTGCG AGGGGGTAGA AAAGGAAAGG GGCGTGTTGA TGTTGGCGGA GTTGTCGAGT
 G  V   V   E   G   L   K   R   G   A   E   G   V   E   K   E   R   G   V   L   M   L   A   E   L   S>

1130         1140         1150         1160         1170         1180         1190         1200
AAAGGCTCGT TGGCCATGGG TGAATATACC CGTGAGACGA TCGAGATTGC GAAGAGTGAT CGGGAGTTCG TGATTGGGTT
 K  G   S   L   A   H   G   E   Y   T   R   E   T   I   E   I   A   K   S   D   R   E   F   V   I   G   F>
```

FIG. 2 (cont'd.)

```
       1210       1220       1230       1240       1250       1260       1270       1280
CATCGCGCAG CGGGACATGG GGGTAGAGA AGAAGGGTTT GATTGGATCA TCATGACGCC TGGTGTGGGG TTGGATGATA
 I  A  Q    R  D  M    G  G  R  E    E  G  F    D  W  I    I  M  T  P    G  V  G    L  D  D>

1290       1300       1310       1320       1330       1340       1350       1360
AAGGCGATGC GTTGGGCCAG CAGTATAGGA CTGTTGATGA GGTGGTTCTG ACTGGTACCG ATGTGATTAT TGTCGGGAGA
 K  G  D  A    L  G  Q    Q  Y  R    T  V  D  E    V  V  L    T  G  T    D  V  I  I    V  G  R>

1370       1380       1390       1400       1410       1420       1430       1440
GGGTGTTTG GAAAAGGAAG AGACCCTGAG GTGGAGGAA AGAGATACAG GGATGCTGGA TGGAAGGCAT ACTTGAAGAG
 G  L  F    G  K  G  R    D  P  E    V  E  G    K  R  Y  R    D  A  G    W  K  A    Y  L  K  R>

1450       1460       1470       1480       1490       1500       1510       1520
AACTGGTCAG TTAGAATAAA TATTGTAATA AATAGGTCTA CTAAGCTTCT AGGACGTCAT TGTAGTCTTC
 T  G  Q    L  E  *>

1530       1540       1550       1560       1570       1580       1590       1600
GAAGTTGTCT GCTAGTTTAG TTCTCATGAT TTCGAAAACC AATAACGCAA TGGATGTAGC AGGGATGGTG GTTAGTGCGT 1610       1620       1630       1640       1650       1660       1670       1680
TCCTGACAAA CCCAGAGTAC GCCGCCTCAA ACCACGTCAC ATTCGCCCTT TGCTTCATCC GCATCACTTG CTTGAAGGTA 1690       1700       1710
TCCACGTACG AGTTGTAATA CACCTTGAAG AA
```

FIG. 2 (cont'd.)

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
aggcgcgccc catccaaaag gaaagagaca gc                              32

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
ccttaattaa cgtcaacaat caatctggcg tagac                           35

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
ccttaattaa tcacggttac tcgtcctaca acgg                            34

<210> SEQ ID NO 4
<211> LENGTH: 37
<212> TYPE: DNA
```

```
<213> ORGANISM: Artificial Sequence
<220> FEATURE:
<223> OTHER INFORMATION: primer

<400> SEQUENCE: 4
agctttgttt aaacgcagcg gtttcatcag acttttc                              37

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
ccttaattaa gctcacgagt tttgggattt tc                                   32

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ccttaattaa tggataccct tcaagcaagtg                                     30

<210> SEQ ID NO 7
<211> LENGTH: 2845
<212> TYPE: DNA
<213> ORGANISM: Candida tropicalis
<220> FEATURE:
<221> NAME/KEY: CDS
<222> LOCATION: (532)..(2658)

<400> SEQUENCE: 7
```

| | | |
|---|---|---|
| gagctccaat tgtaatattt cgggagaaat atcgttgggg taaaacaaca gagagagaga | 60 |
| gggagagatg gttctggtag aattataatc tggttgttgc aaatgctact gatcgactct | 120 |
| ggcaatgtct gtagctcgct agttgtatgc aacttaggtg ttatgcatac acacggttat | 180 |
| tcggttgaat tgtggagtaa aaattgtctg agttgtgtct tagctactgg ctggcccccc | 240 |
| gcgaaagata atcaaaatta cacttgtgaa ttttgcaca cacaccgatt aacatttccc | 300 |
| ttttttgtcc accgatacac gcttgcctct tcttttttt ctctgtgctt cccctcctg | 360 |
| tgacttttc caccattgat ataaaatcaa ctccatttcc ctaaaatctc cccagattct | 420 |
| aaaaacaact tcttctcttc tgcttttcct ttttttttgt tatatttatt taccatccct | 480 |
| ttttttgaa tagttattcc ccactaacat tgttcaaatc ttcacgacat a atg act | 537 |
|                                                                 Met Thr |
|                                                                   1 |

| | | |
|---|---|---|
| ttt aca aag aaa aac gtt agt gta tca caa ggt cct gac cct aga tca | 585 |
| Phe Thr Lys Lys Asn Val Ser Val Ser Gln Gly Pro Asp Pro Arg Ser | |
|     5                   10                  15 | |

| | | |
|---|---|---|
| tcc atc caa aag gaa aga gac agc tcc aaa tgg aac cct caa caa atg | 633 |
| Ser Ile Gln Lys Glu Arg Asp Ser Ser Lys Trp Asn Pro Gln Gln Met | |
|  20                  25                  30 | |

| | | |
|---|---|---|
| aac tac ttc ttg gaa ggc tcc gtc gaa aga agt gag ttg atg aag gct | 681 |
| Asn Tyr Phe Leu Glu Gly Ser Val Glu Arg Ser Glu Leu Met Lys Ala | |
| 35                  40                  45                  50 | |

| | | |
|---|---|---|
| ttg gcc caa caa atg gaa aga gac cca atc ttg ttc aca gac ggc tcc | 729 |
| Leu Ala Gln Gln Met Glu Arg Asp Pro Ile Leu Phe Thr Asp Gly Ser | |
|             55                  60                  65 | |

-continued

| | |
|---|---|
| tac tac gac ttg acc aag gac caa caa aga gaa ttg acc gcc gtc aag<br>Tyr Tyr Asp Leu Thr Lys Asp Gln Gln Arg Glu Leu Thr Ala Val Lys<br>          70                         75                         80 | 777 |
| atc aac aga atc gcc aga tac aga gaa caa gaa tcc atc gac act ttc<br>Ile Asn Arg Ile Ala Arg Tyr Arg Glu Gln Glu Ser Ile Asp Thr Phe<br>         85                        90                       95 | 825 |
| aac aag aga ttg tcc ttg att ggt atc ttt gac cca cag gtc ggt acc<br>Asn Lys Arg Leu Ser Leu Ile Gly Ile Phe Asp Pro Gln Val Gly Thr<br>      100                    105                    110 | 873 |
| aga att ggt gtc aac ctc ggt ttg ttc ctt tct tgt atc aga ggt aac<br>Arg Ile Gly Val Asn Leu Gly Leu Phe Leu Ser Cys Ile Arg Gly Asn<br>115                    120                    125                    130 | 921 |
| ggt acc act tcc caa ttg aac tac tgg gct aac gaa aag gaa acc gct<br>Gly Thr Thr Ser Gln Leu Asn Tyr Trp Ala Asn Glu Lys Glu Thr Ala<br>                 135                    140                    145 | 969 |
| gac gtt aaa ggt atc tac ggt tgt ttc ggt atg acc gaa ttg gcc cac<br>Asp Val Lys Gly Ile Tyr Gly Cys Phe Gly Met Thr Glu Leu Ala His<br>             150                    155                    160 | 1017 |
| ggt tcc aac gtt gct ggt ttg gaa acc acc gcc aca ttt gac aag gaa<br>Gly Ser Asn Val Ala Gly Leu Glu Thr Thr Ala Thr Phe Asp Lys Glu<br>         165                    170                    175 | 1065 |
| tct gac gag ttt gtc atc aac acc cca cac att ggt gcc acc aag tgg<br>Ser Asp Glu Phe Val Ile Asn Thr Pro His Ile Gly Ala Thr Lys Trp<br>180                    185                    190 | 1113 |
| tgg att ggt ggt gct gct cac tcc gcc acc cac tgt tct gtc tac gcc<br>Trp Ile Gly Gly Ala Ala His Ser Ala Thr His Cys Ser Val Tyr Ala<br>195                    200                    205                    210 | 1161 |
| aga ttg att gtt gac ggt caa gat tac ggt gtc aag act ttt gtt gtc<br>Arg Leu Ile Val Asp Gly Gln Asp Tyr Gly Val Lys Thr Phe Val Val<br>                 215                    220                    225 | 1209 |
| cca ttg aga gac tcc aac cac gac ctc atg cca ggt gtc act gtt ggt<br>Pro Leu Arg Asp Ser Asn His Asp Leu Met Pro Gly Val Thr Val Gly<br>             230                    235                    240 | 1257 |
| gac att ggt gcc aag atg ggt aga gat ggt atc gat aac ggt tgg atc<br>Asp Ile Gly Ala Lys Met Gly Arg Asp Gly Ile Asp Asn Gly Trp Ile<br>         245                    250                    255 | 1305 |
| caa ttc tcc aac gtc aga atc cca aga ttc ttt atg ttg caa aag ttc<br>Gln Phe Ser Asn Val Arg Ile Pro Arg Phe Phe Met Leu Gln Lys Phe<br>260                    265                    270 | 1353 |
| tgt aag gtt tct gct gaa ggt gaa gtc acc ttg cca cct ttg gaa caa<br>Cys Lys Val Ser Ala Glu Gly Glu Val Thr Leu Pro Pro Leu Glu Gln<br>275                    280                    285                    290 | 1401 |
| ttg tct tac tcc gcc ttg ttg ggt ggt aga gtc atg atg gtt ttg gac<br>Leu Ser Tyr Ser Ala Leu Leu Gly Gly Arg Val Met Met Val Leu Asp<br>                 295                    300                    305 | 1449 |
| tcc tac aga atg ttg gct aga atg tcc acc att gcc ttg aga tac gcc<br>Ser Tyr Arg Met Leu Ala Arg Met Ser Thr Ile Ala Leu Arg Tyr Ala<br>             310                    315                    320 | 1497 |
| att ggt aga aga caa ttc aag ggt gac aat gtc gat cca aaa gat cca<br>Ile Gly Arg Arg Gln Phe Lys Gly Asp Asn Val Asp Pro Lys Asp Pro<br>         325                    330                    335 | 1545 |
| aac gct ttg gaa acc caa ttg ata gat tac cca ttg cac caa aag aga<br>Asn Ala Leu Glu Thr Gln Leu Ile Asp Tyr Pro Leu His Gln Lys Arg<br>340                    345                    350 | 1593 |
| ttg ttc cca tac ttg gct gct gcc tac gtc atc tcc gct ggt gcc ctc<br>Leu Phe Pro Tyr Leu Ala Ala Ala Tyr Val Ile Ser Ala Gly Ala Leu<br>355                    360                    365                    370 | 1641 |
| aag gtt gaa gac acc atc cat aac acc ttg gct gaa ttg gac gct gcc<br>Lys Val Glu Asp Thr Ile His Asn Thr Leu Ala Glu Leu Asp Ala Ala<br>                 375                    380                    385 | 1689 |

-continued

| | | |
|---|---|---|
| gtt gaa aag aac gac acc aag gct atc ttt aag tct att gac gac atg<br>Val Glu Lys Asn Asp Thr Lys Ala Ile Phe Lys Ser Ile Asp Asp Met<br>390                           395                      400 | 1737 |
| aag tca ttg ttt gtt gac tct ggt tcc ttg aag tcc act gcc act tgg<br>Lys Ser Leu Phe Val Asp Ser Gly Ser Leu Lys Ser Thr Ala Thr Trp<br>     405                      410                      415 | 1785 |
| ttg ggt gct gaa gcc att gac caa tgt aga caa gcc tgt ggt ggt cac<br>Leu Gly Ala Glu Ala Ile Asp Gln Cys Arg Gln Ala Cys Gly Gly His<br>420                           425                      430 | 1833 |
| ggt tac tcg tcc tac aac ggc ttc ggt aaa gcc tac aac gat tgg gtt<br>Gly Tyr Ser Ser Tyr Asn Gly Phe Gly Lys Ala Tyr Asn Asp Trp Val<br>435                           440                      445                      450 | 1881 |
| gtc caa tgt act tgg gaa ggt gac aac aat gtc ttg gcc atg agt gtt<br>Val Gln Cys Thr Trp Glu Gly Asp Asn Asn Val Leu Ala Met Ser Val<br>                      455                      460                      465 | 1929 |
| ggt aag cca att gtc aag caa gtt atc agc att gaa gat gcc ggc aag<br>Gly Lys Pro Ile Val Lys Gln Val Ile Ser Ile Glu Asp Ala Gly Lys<br>470                           475                      480 | 1977 |
| acc gtc aga ggt tcc acc gct ttc ttg aac caa ttg aag gac tac act<br>Thr Val Arg Gly Ser Thr Ala Phe Leu Asn Gln Leu Lys Asp Tyr Thr<br>     485                      490                      495 | 2025 |
| ggt tcc aac agc tcc aag gtt gtt ttg aac act gtt gct gac ttg gac<br>Gly Ser Asn Ser Ser Lys Val Val Leu Asn Thr Val Ala Asp Leu Asp<br>500                           505                      510 | 2073 |
| gac atc aag act gtc atc aag gct att gaa gtt gcc atc atc aga ttg<br>Asp Ile Lys Thr Val Ile Lys Ala Ile Glu Val Ala Ile Ile Arg Leu<br>515                           520                      525                      530 | 2121 |
| tcc caa gaa gct gct tct att gtc aag aag gaa tct ttc gac tat gtc<br>Ser Gln Glu Ala Ala Ser Ile Val Lys Lys Glu Ser Phe Asp Tyr Val<br>                      535                      540                      545 | 2169 |
| ggc gct gaa ttg gtt caa ctc tcc aag ttg aag gct cac cac tac ttg<br>Gly Ala Glu Leu Val Gln Leu Ser Lys Leu Lys Ala His His Tyr Leu<br>           550                      555                      560 | 2217 |
| ttg act gaa tac atc aga aga att gac acc ttt gac caa aag gac ttg<br>Leu Thr Glu Tyr Ile Arg Arg Ile Asp Thr Phe Asp Gln Lys Asp Leu<br>     565                      570                      575 | 2265 |
| gtt cca tac ttg atc acc ctc ggt aag ttg tac gct gcc act att gtc<br>Val Pro Tyr Leu Ile Thr Leu Gly Lys Leu Tyr Ala Ala Thr Ile Val<br>580                           585                      590 | 2313 |
| ttg gac aga ttt gcc ggt gtc ttc ttg act ttc aac gtt gcc tcc acc<br>Leu Asp Arg Phe Ala Gly Val Phe Leu Thr Phe Asn Val Ala Ser Thr<br>595                           600                      605                      610 | 2361 |
| gaa gcc atc act gct ttg gcc tct gtg caa att cca aag ttg tgt gct<br>Glu Ala Ile Thr Ala Leu Ala Ser Val Gln Ile Pro Lys Leu Cys Ala<br>                      615                      620                      625 | 2409 |
| gaa gtc aga cca aac gtt gtt gct tac acc gac tcc ttc caa caa tcc<br>Glu Val Arg Pro Asn Val Val Ala Tyr Thr Asp Ser Phe Gln Gln Ser<br>           630                      635                      640 | 2457 |
| gac atg att gtc aat tct gct att ggt aga tac gat ggt gac atc tat<br>Asp Met Ile Val Asn Ser Ala Ile Gly Arg Tyr Asp Gly Asp Ile Tyr<br>                645                      650                      655 | 2505 |
| gag aac tac ttt gac ttg gtc aag ttg cag aac cca cca tcc aag acc<br>Glu Asn Tyr Phe Asp Leu Val Lys Leu Gln Asn Pro Pro Ser Lys Thr<br>660                           665                      670 | 2553 |
| aag gct cct tac tct gat gct ttg gaa gcc atg ttg aac aga cca acc<br>Lys Ala Pro Tyr Ser Asp Ala Leu Glu Ala Met Leu Asn Arg Pro Thr<br>675                           680                      685                      690 | 2601 |
| ttg gac gaa aga gaa aga ttt gaa aag tct gat gaa acc gct gct atc<br>Leu Asp Glu Arg Glu Arg Phe Glu Lys Ser Asp Glu Thr Ala Ala Ile | 2649 |

```
                    695             700             705
ttg tcc aag taagaataga agagagtgac tcttttgata agagtcgcaa        2698
Leu Ser Lys atttgatttc ataagtatat attcattatg taaagtagta aatggaaaat tcattaaaaa   2758
aaaagcaaat ttccgttgta tgcatactcc gaacacaaaa ctagccccgg aaaaacccct   2818
agttgatagt tgcgaattta ggtcgac                                       2845

<210> SEQ ID NO 8
<211> LENGTH: 709
<212> TYPE: PRT
<213> ORGANISM: Candida tropicalis

<400> SEQUENCE: 8

Met Thr Phe Thr Lys Lys Asn Val Ser Val Ser Gln Gly Pro Asp Pro
1               5                   10                  15

Arg Ser Ser Ile Gln Lys Glu Arg Asp Ser Ser Lys Trp Asn Pro Gln
                20                  25                  30

Gln Met Asn Tyr Phe Leu Glu Gly Ser Val Glu Arg Ser Glu Leu Met
            35                  40                  45

Lys Ala Leu Ala Gln Gln Met Glu Arg Asp Pro Ile Leu Phe Thr Asp
50                  55                  60

Gly Ser Tyr Tyr Asp Leu Thr Lys Asp Gln Gln Arg Glu Leu Thr Ala
65                  70                  75                  80

Val Lys Ile Asn Arg Ile Ala Arg Tyr Arg Glu Gln Glu Ser Ile Asp
                85                  90                  95

Thr Phe Asn Lys Arg Leu Ser Leu Ile Gly Ile Phe Asp Pro Gln Val
            100                 105                 110

Gly Thr Arg Ile Gly Val Asn Leu Gly Leu Phe Leu Ser Cys Ile Arg
        115                 120                 125

Gly Asn Gly Thr Thr Ser Gln Leu Asn Tyr Trp Ala Asn Glu Lys Glu
130                 135                 140

Thr Ala Asp Val Lys Gly Ile Tyr Gly Cys Phe Gly Met Thr Glu Leu
145                 150                 155                 160

Ala His Gly Ser Asn Val Ala Gly Leu Glu Thr Thr Ala Thr Phe Asp
                165                 170                 175

Lys Glu Ser Asp Glu Phe Val Ile Asn Thr Pro His Ile Gly Ala Thr
            180                 185                 190

Lys Trp Trp Ile Gly Gly Ala Ala His Ser Ala Thr His Cys Ser Val
        195                 200                 205

Tyr Ala Arg Leu Ile Val Asp Gly Gln Asp Tyr Gly Val Lys Thr Phe
210                 215                 220

Val Val Pro Leu Arg Asp Ser Asn His Asp Leu Met Pro Gly Val Thr
225                 230                 235                 240

Val Gly Asp Ile Gly Ala Lys Met Gly Arg Asp Gly Ile Asp Asn Gly
                245                 250                 255

Trp Ile Gln Phe Ser Asn Val Arg Ile Pro Arg Phe Phe Met Leu Gln
            260                 265                 270

Lys Phe Cys Lys Val Ser Ala Glu Gly Glu Val Thr Leu Pro Pro Leu
        275                 280                 285

Glu Gln Leu Ser Tyr Ser Ala Leu Leu Gly Gly Arg Val Met Met Val
290                 295                 300

Leu Asp Ser Tyr Arg Met Leu Ala Arg Met Ser Thr Ile Ala Leu Arg
305                 310                 315                 320
```

```
Tyr Ala Ile Gly Arg Gln Phe Lys Gly Asp Asn Val Asp Pro Lys
                325                 330                 335

Asp Pro Asn Ala Leu Glu Thr Gln Leu Ile Asp Tyr Pro Leu His Gln
            340                 345                 350

Lys Arg Leu Phe Pro Tyr Leu Ala Ala Tyr Val Ile Ser Ala Gly
        355                 360                 365

Ala Leu Lys Val Glu Asp Thr Ile His Asn Thr Leu Ala Glu Leu Asp
370                 375                 380

Ala Ala Val Glu Lys Asn Asp Thr Lys Ala Ile Phe Lys Ser Ile Asp
385                 390                 395                 400

Asp Met Lys Ser Leu Phe Val Asp Ser Gly Ser Leu Lys Ser Thr Ala
                405                 410                 415

Thr Trp Leu Gly Ala Glu Ala Ile Asp Gln Cys Arg Gln Ala Cys Gly
                420                 425                 430

Gly His Gly Tyr Ser Ser Tyr Asn Gly Phe Gly Lys Ala Tyr Asn Asp
            435                 440                 445

Trp Val Val Gln Cys Thr Trp Glu Gly Asp Asn Asn Val Leu Ala Met
        450                 455                 460

Ser Val Gly Lys Pro Ile Val Lys Gln Val Ile Ser Ile Glu Asp Ala
465                 470                 475                 480

Gly Lys Thr Val Arg Gly Ser Thr Ala Phe Leu Asn Gln Leu Lys Asp
                485                 490                 495

Tyr Thr Gly Ser Asn Ser Ser Lys Val Val Leu Asn Thr Val Ala Asp
                500                 505                 510

Leu Asp Asp Ile Lys Thr Val Ile Lys Ala Ile Glu Val Ala Ile Ile
            515                 520                 525

Arg Leu Ser Gln Glu Ala Ala Ser Ile Val Lys Lys Glu Ser Phe Asp
530                 535                 540

Tyr Val Gly Ala Glu Leu Val Gln Leu Ser Lys Leu Lys Ala His His
545                 550                 555                 560

Tyr Leu Leu Thr Glu Tyr Ile Arg Arg Ile Asp Thr Phe Asp Gln Lys
                565                 570                 575

Asp Leu Val Pro Tyr Leu Ile Thr Leu Gly Lys Leu Tyr Ala Ala Thr
            580                 585                 590

Ile Val Leu Asp Arg Phe Ala Gly Val Phe Leu Thr Phe Asn Val Ala
        595                 600                 605

Ser Thr Glu Ala Ile Thr Ala Leu Ala Ser Val Gln Ile Pro Lys Leu
610                 615                 620

Cys Ala Glu Val Arg Pro Asn Val Val Ala Tyr Thr Asp Ser Phe Gln
625                 630                 635                 640

Gln Ser Asp Met Ile Val Asn Ser Ala Ile Gly Arg Tyr Asp Gly Asp
                645                 650                 655

Ile Tyr Glu Asn Tyr Phe Asp Leu Val Lys Leu Gln Asn Pro Pro Ser
            660                 665                 670

Lys Thr Lys Ala Pro Tyr Ser Asp Ala Leu Glu Ala Met Leu Asn Arg
        675                 680                 685

Pro Thr Leu Asp Glu Arg Glu Arg Phe Glu Lys Ser Asp Glu Thr Ala
690                 695                 700

Ala Ile Leu Ser Lys
705

<210> SEQ ID NO 9
<211> LENGTH: 1712
<212> TYPE: DNA
```

```
<213> ORGANISM: Candida tropicalis

<400> SEQUENCE: 9
ggtaccgagc tcacgagttt tgggattttc gagtttggat tgtttccttt gttgattgaa      60
ttgacgaaac cagaggtttt caagacagat aagattgggt ttatcaaaac gcagtttgaa     120
atattccagt tggtttccaa gatatcttga agaagattga cgatttgaaa tttgaagaag     180
tggagaagat ctggtttgga ttgttggaga atttcaagaa tctcaagatt tactctaacg     240
acgggtacaa cgagaattgt attgaattga tcaagaacat gatcttggtg ttacagaaca     300
tcaagttctt ggaccagact gagaatgcca cagatataca aggcgtcatg tgataaaatg     360
gatgagattt atcccacaat tgaagaaaga gtttatggaa agtggtcaac cagaagctaa     420
acaggaagaa gcaaacgaag aggtgaaaca agaagaagaa ggtaaataag tattttgtat     480
tatataacaa acaaagtaag gaatacagat ttatacaata aattgccata ctagtcacgt     540
gagatatctc atccattccc caactcccaa gaaaaaaaaa aagtgaaaaa aaaaatcaaa     600
cccaaagatc aacctcccca tcatcatcgt catcaaaccc ccagctcaat tcgcaatggt     660
tagcacaaaa acatacacag aaagggcatc agcacacccc tccaaggttg cccaacgttt     720
attccgctta atggagtcca aaaagaccaa cctctgcgcc tcgatcgacg tgaccacaac     780
cgccgagttc ctttcgctca tcgacaagct cggtccccac atctgtctcg tgaagacgca     840
catcgatatc atctcagact tcagctacga gggcacgatt gagccgttgc ttgtgcttgc     900
agagcgccac gggttcttga tattcgagga caggaagttt gctgatatcg aaacaccgt      960 gatgttgcag tacacctcgg gggtataccg gatcgcggcg tggagtgaca tcacgaacgc    1020
gcacggagtg actgggaagg gcgtcgttga agggttgaaa cgcggtgcgg aggggtaga     1080 aaaggaaagg ggcgtgttga tgttggcgga gttgtcgagt aaaggctcgt tggcgcatgg    1140
tgaatatacc cgtgagacga tcgagattgc gaagagtgat cgggagttcg tgattgggtt    1200
catcgcgcag cgggacatgg ggggtagaga agaagggttt gattggatca tcatgacgcc    1260
tggtgtgggg ttggatgata aaggcgatgc gttgggccag cagtatagga ctgttgatga    1320
ggtggttctg actggtaccg atgtgattat tgtcgggaga gggttgtttg gaaaaggaag    1380
agaccctgag gtggagggaa agagatacag ggatgctgga tggaaggcat acttgaagag    1440
aactggtcag ttagaataaa tattgtaata aataggtcta tatacataca ctaagcttct    1500
aggacgtcat tgtagtcttc gaagttgtct gctagtttag ttctcatgat ttcgaaaacc    1560
aataacgcaa tggatgtagc agggatggtg gttagtgcgt tcctgacaaa cccagagtac    1620
gccgcctcaa accacgtcac attcgccctt tgcttcatcc gcatcacttg cttgaaggta    1680
tccacgtacg agttgtaata caccttgaag aa                                  1712
```

NON-REVERTIBLE β-OXIDATION BLOCKED *CANDIDA TROPICALIS*

CROSS REFERENCE TO RELATED APPLICATIONS

The present application is a continuation of copending U.S. application Ser. No. 10/444,467, filed May 22, 2003, which claims benefit under 35 U.S.C. §119(e) of earlier filed and U.S. Provisional Application Ser. No. 60/383,332 filed May 23, 2002, the contents of each of which are incorporated by reference herein.

STATEMENT REGARDING FEDERAL SPONSORED RESEARCH OR DEVELOPMENT

This invention was funded, at least in part, under grants from the Department of Commerce, NIST-ATP Cooperative Agreement Number 70NANB8H4033. The Government may therefore have certain rights in the invention.

BACKGROUND OF THE INVENTION

Aliphatic dioic acids are versatile chemical intermediates useful as raw materials for the preparation of perfumes, polymers, adhesives and macrolid antibiotics. While several chemical routes for the synthesis of long-chain α,ω-dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the most commercially viable route, due to limitations with the current biological approaches.

Several strains of yeast are known to excrete α,ω-dicarboxylic acids as a byproduct when cultured on alkanes or fatty acids as the carbon source. In particular, yeast belonging to the Genus *Candida*, such as *C. albicans, C. cloacae, C. guillermondii, C. intermedia, C. lipolytica, C. maltosa, C. parapsilosis* and *C. zeylenoides* are known to produce such dicarboxylic acids (*Agr. Biol. Chem.* 35: 2033-2042 (1971)). Also, various strains of *C. tropicalis* are known to produce dicarboxylic acids ranging in chain lengths from $C_{11}$ through $C_{18}$ (Okino et al., "Production of Macrocyclic Musk Compounds via Alkanedioic Acids Produced From N-Alkanes", from Lawrence, et al. (eds.), *Flavors and Fragrances: A World Perspective*. Proceedings of the $10^{th}$ International Conference of Essential Oils, Flavors and Fragrances, Elsevier Science Publishers BV Amsterdam, pp. 753-760 (1988)), and are the basis of several patents as reviewed by Bühler and Schindler, in *Aliphatic Hydrocarbons in Biotechnology*, H. J. Rehm and G. Reed (eds.), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, ω-oxidation of fatty acids to α,ω-dicarboxylic acids, and the degradative β-oxidation of fatty acids to $CO_2$ and water. The first two types of oxidations are catalyzed by microsomal enzymes while the last type takes place in the peroxisomes. In *C. tropicalis*, the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids as described, e.g., in Gilewicz et al., *Can. J. Microbiol.* 25:201 (1979), incorporated herein by reference. The genes which encode the cytochrome P450 and NADPH reductase components of the complex have previously been identified as P450ALK and P450RED respectively, and have also been cloned and sequenced as described, e.g., in Sanglard et al., *Gene* 76:121-136 (1989), incorporated herein by reference. P450ALK has also been designated P450ALK1. More recently, ALK genes have been designated by the symbol CYP and RED genes have been designated by the symbol CPR. See, e.g., Nelson, *Pharmacogenetics* 6(1):1-42 (1996), which is incorporated herein by reference. See also Ohkuma et al., *DNA and Cell Biology* 14:163-173 (1995), Seghezzi et al., *DNA and Cell Biology*, 11:767-780 (1992) and Kargel et al., *Yeast* 12:333-348 (1996), each incorporated herein by reference. In addition, CPR genes are now also referred to as NCP genes. See, e.g., De Backer et al., *Antimicrobial Agents and Chemotherapy*, 45:1660 (2001). For example, P450ALK is also designated CYP52 according to the nomenclature of Nelson, supra.

Fatty acids are ultimately formed from alkanes after two additional oxidation steps, catalyzed by alcohol oxidase as described, e.g., in Kemp et al., *Appl. Microbiol. and Biotechnol.* 28: 370-374 (1988), incorporated herein by reference, and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.*, 102:225-234 (1987)). In yeast, β-oxidation takes place solely in the peroxisomes (*Agr. Biol. Chem.* 49:1821-1828 (1985)).

The dicarboxylic acids produced through fermentation by most yeasts, including *C. tropicalis*, are most often shorter than the original substrate by one or more pairs of carbon atoms and mixtures are common (Ogino et al., "Studies of Utilization of Hydrocarbons by Yeasts Part II. Diterminal Oxidation of Alkanes by Yeast", *Agr. Biol. Chem.*, Vol. 29, No. 11, pp. 1009-1015 (1965); Shiio et al. "Microbial Production of Long-chain Dicarboxylic Acids from n-Alkanes, Part I. Screening and Properties of Microorganism Producing Dicarboxylic Acids", *Agr. Biol. Chem.*, Vol. 35, No. 13, pp. 2033-2012 (1971); Rehm et al. "Mechanisms and Occurrence of Microbial Oxidation of Long-chain Alkanes", *Institute for Microbiologie*, pp. 176-217 (1980); Hill et al., "Studies on the Formation of Long-chain Dicarboxylic Acids from Pure n-alkanes by a Mutant of *Candida tropicalis*", *Appl. Microbiol. Biotechnol.*, 24:168-174 (1986). This is due to the degradation of the substrate and product by the peroxisomal β-oxidation pathway. This series of enzymatic reactions leads to the progressive shortening of the activated acyl-CoA through the cleavage of 2 carbon acetyl-CoA moieties in a cyclic manner. The initial step in the pathway, involving oxidation of the acyl-CoA to its enoyl-CoA derivative, is catalyzed by acyl-CoA oxidase. The enoyl-CoA is further metabolized to the β-keto acid by the action of enoyl-CoA hydratase and 3-hydroxyacyl-CoA dehydrogenase as a prerequisite to the cleavage between the α and β carbons by 3-ketoacyl-CoA thiolase. Mutations causing partial blockage of these latter reactions result in the formation of unsaturated or 3-hydroxymonocarboxylic or 3-hydroxy-dicarboxylic acids (Meussdoeffer, 1988). These undesirable by-products are often associated with biological production of dicarboxylic acids.

It is known that the formation of dioic acids can be substantially increased by the use of suitable mutants (Shiio et al., supra; Furukawa et al., "Selection of High Brassylic Acid Producing Strains of *Torulopsis candida* by Single-Cell Cloning and by Mutation", *J. Ferment. Technol.*, Vol. 64, No. 2, pp. 97-101 (1986); Hill et al., supra; Okino et al., supra). While the wild-type yeasts produce little if any dicarboxylic acids, mutants partially defective in their ability to grow on alkane, fatty acid or dicarboxylic acid substrates often demonstrate enhanced dicarboxylic acid yields. However, these mutants have not been characterized beyond their reduced ability to utilize these compounds as a carbon source for growth. In all likelihood, their ability to produce dicarboxylic acids is enhanced by a partial blockage of the β-oxidation pathway. It is also known that compounds known to inhibit β-oxidation (i.e. acrylate) also result in increased dicarboxylic acid yields. Jianlong et al., "The Regulation of Alanine on the Fermentation of Long-Chain Dicarboxylic Acids in *Candida tropicalis* NPcoN22", p. 4 (1988).

β-oxidation blocked *C. tropicalis* strains, such as H5343 (ATCC No. 20962) are disclosed in U.S. Pat. No. 5,254,466, the entire contents of which are incorporated herein by reference. These *C. tropicalis* strains have disrupted chromosomal POX 4A, POX 4B and both POX 5 genes. The disruption of the POX genes was performed by insertional disruption in which the URA 3 nutritional marker was inserted into a construct containing the gene(s) encoding the acyl CoA oxidase, POX 4 or POX 5, and transformed into the target organism. Homologous recombination yielded organisms that were disrupted for POX 4 and POX 5.

The POX 4 and POX 5 genes encode distinct subunits of long chain acyl-CoA oxidase, which are the peroxisomal polypeptides (PXPs) designated PXP-4 and PXP-5, respectively. The disruption of the POX 4 and POX 5 genes encoding these PXPs effectively blocks the β-oxidation pathway at its first reaction (which is catalyzed by acyl-CoA oxidase), thereby redirecting the substrate toward the ω-oxidation pathway while preventing the degradation and/or reutilization of the dicarboxylic acid products by the β-oxidation pathway. Therefore, a *C. tropicalis* strain in which all four POX genes are disrupted will synthesize substantially pure α,ω-dicarboxylic acids with increased quantitative yield because the biosynthetic pathway which produces undesirable chain modifications associated with passage through the β-oxidation pathway, such as unsaturation, hydroxylation, or chain shortening, is no longer functional.

*C. tropicalis* strains may also have one or more cytochrome P450 (P450ALK) genes and/or reductase (P450RED) genes amplified, which results in an increase in the amount of rate-limiting ω-hydroxylase through P450 gene amplification and increases the rate of substrate flow through the ω-oxidation pathway. Specific examples of CPR (reductase) genes include the CPRA and CPRB genes of *C. tropicalis* 20336 as described, e.g., in U.S. Pat. No. 6,331,420 and International Application No. PCT/US99/20797, the contents of each of which are incorporated herein by reference. Other known *C. tropicalis* strains include AR40, an amplified 115343 strain wherein all four POX genes are disrupted by a URA 3 selectable marker, which also contains 3 additional copies of the cytochrome P450 gene and 2 additional copies of the reductase gene, the P450RED gene. Strain R24 is an amplified H5343 strain in which all four POX genes are disrupted by a URA 3 selectable marker and which also contains multiple copies of the reductase gene. Strains AR40 and R24 are described in U.S. Pat. Nos. 5,620,878 and 5,648,247, the contents of each of which are incorporated by reference herein.

These strains have been the basis for newly modified strains created and employed for use in the dicarboxylic acid production process for a number of years. However, upon fermentation of fatty acid and/or alkane substrates using β-oxidation blocked yeast strains, such strains have shown reversion at the POX 4 locus. Upon reversion to a wild-type POX 4 gene, the β-oxidation pathway is no longer blocked and a decrease in dicarboxylic acid production results. Therefore, a need exists for improved yeast strains comprising a stable POX 4 disruption that will not revert to wild-type activity.

SUMMARY OF THE INVENTION

Novel yeast strains, having their β-oxidation pathway blocked and a portion of a chromosomal target gene deleted, are disclosed. The deletion of the portion of the chromosomal target gene is of sufficient size that it prevents the strain from reverting to wild-type activity.

In a preferred embodiment, the yeast strain is *C. tropicalis* and the chromosomal target gene is the POX 4 gene or the POX 5 gene. The deletion of a portion of the POX 4 or POX 5 genes results in a non-revertible β-oxidation blocked *C. tropicalis* strain. More preferred embodiments also have disruptions of other genes of the β-oxidation pathway and amplifications of the cytochrome P450 genes and/or reductase genes. The resulting strains thus have both a blocked β-oxidation pathway as well as an increase in the amount of rate-limiting ω-hydroxylase, which increases the rate of substrate flow through the ω-oxidation pathway and results in the production of substantially pure α,ω-dicarboxylic acids.

The POX 4 gene may be POX 4A, POX 4B, or both POX 4A and POX 4B. The POX 5 gene may, in some embodiments, be both copies of the chromosomal POX 5 gene. In some embodiments, the deletion may be to POX 4A, POX 4B, POX 5, both copies of the chromosomal POX 5 gene, or any combination thereof.

Preferably, the deletion of the portion of the chromosomal target gene, i.e., POX 4 or POX 5, occurs by homologous recombination of said POX 4 or POX 5 gene with a DNA fragment comprised of a selectable marker gene flanked on both ends by DNA sequences having homology to said POX 4 or POX 5 gene, but said DNA sequences are not contiguous. The resulting vector is referred to herein as a POX 4-deleted disruption cassette or a POX 5-deleted disruption cassette. The selectable marker is one which confers a particular phenotype to the cell into which the DNA fragment is transformed. More preferably, the selectable marker confers a prototrophic phenotype to transformed cells, such as for a particular pyrimidine, whereby the transformed cells may then be selected by their ability to grow in a medium deficient in the pyrimidine. In a most preferred embodiment the selectable marker gene is URA 3.

In accordance with the present invention, a yeast host cell transformed with a POX4-deleted disruption cassette has its chromosomal POX 4 gene replaced with a partially deleted POX 4 gene. Likewise, a yeast host cell transformed with a POX 5-deleted disruption cassette has its chromosomal POX 5 gene replaced with a partially deleted POX 5 gene. In either case, the resulting yeast strain has its β-oxidation pathway blocked and will not revert to wild-type activity.

In a particularly preferred embodiment, *C. tropicalis* H53 is transformed with a POX 4-deleted disruption cassette comprised of a 1676 bp URA 3 selectable marker gene which contains a 647 bp promoter, 803 bp ORF and 226 bp UTR flanked by two non-contiguous flanking sequences from POX 4. When integrated into the C. tropicalis genome, the POX 4-deleted disruption cassette deletes 653 bp of the POX 4 ORF and inserts the 1676 bp URA 3 selectable marker. The resulting transformed C. tropicalis strains containing the deleted POX 4 alleles in the H53 (pox5/pox5) are called HDC100.

Another aspect of the present invention provides methods for producing transformed yeast strains having their β-oxidation pathway by having a portion of one or more genes of the β-oxidation pathway deleted. Preferably, these strains are produced by transforming yeast host cells with a vector which, after homologous recombination with the yeast genome, results in a deletion of a portion of a target gene in the host cell. More preferably, the target gene is POX 4 or POX 5, and the vectors are referred to as a POX 4-deleted disruption cassette or a POX 5-deleted disruption cassette, respectively. A POX 4-deleted disruption cassette comprises a DNA fragment having homology to a portion of the POX 4 gene, a selectable marker gene, and a DNA fragment having homology to a different portion of the POX 4 gene. A POX 5-deleted disruption cassette comprises a DNA fragment having homology to a portion of the POX 5 gene, a selectable marker gene, and a DNA fragment having homology to a different portion of the POX 5 gene. A yeast host cell transformed with a POX 4-deleted disruption cassette has its chromosomal POX 4 gene replaced with a partially deleted POX 4 gene and the selectable marker gene. Likewise, a yeast host cell transformed with a POX 5-deleted disruption cassette as described has its chromosomal POX 5 gene replaced with a partially deleted POX 5 gene and the selectable marker gene.

Yet another aspect of the present invention provides a method of increasing the specific productivity of substantially pure α,ω-dicarboxylic acids in increased quantitative yield by fermenting culture media with a transformed yeast strain having its β-oxidation pathway blocked and a portion of a chromosomal target gene deleted. In preferred embodiment, the transformed yeast strain comprises a C. tropicalis host having a portion of its POX 4 gene deleted. In some embodiments, the C. tropicalis strain may have all of its POX 4 and POX 5 genes disrupted, including the deletion of a portion of the POX 4 gene, and may also have one or more cytochrome P450 (P450ALK) genes and/or reductase (P450RED) genes amplified. Preferably, the culture medium contains a nitrogen source, an organic substrate and a cosubstrate. In a more preferred embodiment, the nitrogen source of the culture medium is an inorganic or organic source of nitrogen normally used in processes for culturing microorganisms; the organic substrate is an aliphatic compound wherein at least one terminal carbon of the aliphatic compound is a methyl group and the aliphatic compound has from about 4 to about 22 carbon atoms; and the cosbustrate is selected from the group consisting of glucose, fructose, maltose, glycerol and sodium acetate.

BRIEF DESCRIPTION OF THE FIGURES

FIG. 1 shows the complete DNA sequence including regulatory and coding regions for the POX4 gene of C. tropicalis (SEQ ID NO:7 and SEQ ID NO:8).

FIG. 2 is the complete DNA sequence encoding URA3A from C. tropicalis ATCC20336 (SEQ ID NO:9).

DETAILED DESCRIPTION OF THE INVENTION

The present invention provides improved yeast strains possessing blocked β-oxidation pathways. The subject yeast strains have a portion of one or more genes of the β-oxidation pathway deleted and are an improvement in the art since reversion to wild-type activity is avoided. Preferably, the yeast strains belong to the Genus Candida. Examples of Candida species that may be used in accordance with the present invention include, but are not limited to, C. albicans, C. cloacae, C. guillermondii, C. intermedia, C. lipolytica, C. maltosa, C. parapsilosis and C. zeylenoides. In a more preferred embodiment, the yeast is C. tropicalis.

In one embodiment, the present invention comprises yeast strains possessing a deletion of the chromosomal POX 4 gene. The size of the deletion may vary, but is sufficient to prevent reversion to wild-type activity at the POX 4 locus once the yeast strain is subjected to the stresses of fermentation. While the deletion could comprise as little as 1 (one) nucleotide, preferably the yeast strain has from about 400 to about 900 nucleotides, or base pairs (bp), of the POX 4 gene deleted. More preferably, a subject yeast strain possesses a deletion of the POX 4 gene of about 500 to about 800 bp. Even more preferably, the deletion comprises about 650 bp of the POX4 gene. In a most preferred embodiment, the deletion is a 653 bp sequence from the POX 4 gene corresponding to nucleotides 1178-1829 of the POX 4 gene sequence (See FIG. 1).

The improved yeast strains of the present invention are produced by transforming yeast host cells with a vector which, after homologous recombination with the yeast genome, results in a deletion of a portion of a target gene in the host cell. For example, a POX 4-deleted disruption cassette may be used to replace a yeast chromosomal POX 4 gene. Likewise, a POX 5-deleted disruption cassette may be used to replace a yeast chromosomal POX 5 gene.

A vector is defined as any linear or circular nucleic acid molecule capable of introducing a foreign nucleic acid molecule into a host cell. Preferably, the vector is an integrating vector. An integrating vector is one which has a nucleic acid sequence with homology to a target site in the genome of the host cell so that vector nucleic acids may be integrated into the nuclear DNA of the host cell.

Linear DNA vectors may be advantageous when it is desirable to avoid introduction of non-native (foreign) DNA into the cell. For example, DNA consisting of a desired target gene(s) flanked by DNA sequences which are native to the cell may be introduced into the cell by electroporation, lithium acetate transformation, spheroplasting, and the like. Flanking DNA sequences may include selectable markers and/or other tools for genetic engineering.

In order to produce a non-revertible β-oxidation blocked yeast strain, an integrating vector with homology to a target site in the genome of the host cell may be used. Preferably, the nucleic acid sequence contained in the vector will include a selectable marker gene, a non-functional copy, or copies, of which may also be present in the nuclear DNA of the host. The fact that the nucleic acid sequence in the vector has homology to some portion of the host's genome makes it integratable into the genome in the region of homology. More preferably, the nucleic acid sequence is DNA. As used herein, the term "integratable" means capable of being inserted into a host genome as a region covalently linked on either side to the host sequences. The region of the host genome into which the nucleic acid sequence from the vector is integrated is defined as the target site. In accordance with the present invention, the target site is a gene which encodes an enzyme involved in the β-oxidation pathway. Preferably the target gene is POX 4 or POX 5. Most preferably, the target gene is POX 4.

The vector used to produce a non-revertible β-oxidation blocked yeast strain comprises a target gene with a deletion contained therein. Such vectors may include serially arranged linear DNA fragments comprised of a DNA fragment which has homology to a gene encoding an enzyme of the β-oxidation pathway in the native yeast genome, a selectable marker gene, and a DNA fragment which has homology to a different portion of the gene encoding an enzyme of the β-oxidation pathway in the native yeast genome. The selectable marker is, therefore, flanked on both ends by DNA sequences which are homologous to a gene in the native yeast genome which encodes an enzyme of the β-oxidation pathway, but which sequences are not contiguous.

For example, a vector may comprise a POX 4-deleted disruption cassette or a POX 5-deleted disruption cassette. A POX 4-deleted disruption cassette comprises a DNA fragment having homology to a portion of a POX 4 gene, a selectable marker gene, and a DNA fragment having homology to a different portion of the POX 4 gene. A POX 5-deleted disruption cassette comprises a DNA fragment having homology to a portion of a POX 5 gene, a selectable marker gene, and a DNA fragment having homology to a different portion of the POX 5 gene. A yeast host cell transformed with a POX 4-deleted disruption cassette as described has its chromosomal POX 4 gene replaced with a partially deleted POX 4 gene. Likewise, a yeast host cell transformed with a POX 5-deleted disruption cassette as described has its chromosomal POX 5 gene replaced with a partially deleted POX 5 gene.

A disruption cassette can be constructed by subcloning a selectable marker into DNA sequences corresponding to a target gene having a deletion. Any type of selectable marker which is extraneous to the target gene may be used. Preferably, the selectable marker is one which confers a particular phenotype to the cell into which the disruption cassette is transformed. Most preferably, the selectable marker confers a prototrophic phenotype to transformed cells which can be reversibly changed to auxotrophy, if desired, so that the same selectable marker may be subsequently used in multiple gene disruptions in the same strain.

For example, a C. tropicalis transformation host which is auxotrophic for a particular pyrimidine may be transformed to prototrophy by a POX 4 or POX 5-deletion disruption cassette containing a functional selectable marker gene required for the synthesis of the particular pyrimidine. The resulting transformants, which have been made prototrophic for said particular pyrimidine, are selected by their ability to grow in a medium deficient in the pyrimidine. These transformants contain a targeted gene deletion as the result of the replacement of a functional target gene with a nonfunctional target gene which includes said deletion.

Where the yeast is C. tropicalis, suitable marker genes include, but are not limited to, URA 3A, URA 3B, or HIS 4 genes. In the case where the selectable marker is a URA gene, a host cell is auxotrophic for uracil; where the selectable marker is a HIS 4 gene, a host cell is auxotrophic for histidine.

In a preferred embodiment, a C. tropicalis transformation host, auxotrophic for uracil (Ura⁻), is transformed to uracil prototrophy with a disruption cassette containing a URA 3 functional gene as the selectable marker. The transformed cells are selected by their ability to grow in the absence of uracil.

In those cases where the yeast transformation host cell is already prototrophic for a specific phenotype, e.g., uracil, confirmation of the pox-phentoype in the resulting transformed strain may be confirmed by the inability of the strain to grow on media containing alkanes, such as decane and dodecane, as the sole carbon source.

Preferably, a significant portion of the open reading frame (ORF) of the target gene, i.e., POX 4, is removed prior to or during the insertion of the selectable marker gene, i.e., URA 3. The selectable marker gene is flanked on one end by a 5'-POX 4 sequence and on the other end by a 3'-POX 4 sequence. The 5'-POX 4 sequence and the 3'-POX 4 sequence are not contiguous and correspond to different portions of the POX 4 gene. Accordingly, transformed cells lack the nucleotides of the POX 4 gene located in the region of the genome between the two POX 4 flanking sequences. By having deleted a portion of the target gene's ORF, removal of the selectable marker gene will not result in reversion to wild-type function, i.e., β-oxidation.

In a particularly preferred embodiment, C. tropicalis H53 may be transformed with a POX 4 disruption cassette comprised of a 1676 bp URA 3 selectable marker gene which contains a 647 bp promoter, 803 bp ORF and 226 bp UTR flanked by two non-contiguous flanking sequences from POX 4. When recombined into the C. tropicalis genome, the POX 4 disruption cassette results in a yeast having a 653 bp deletion in the coding region of the POX 4 ORF, and an insertion of the 1676 bp URA 3 selectable marker. The resulting transformed C. tropicalis strains containing the deleted POX 4 alleles in the H53 (pox5/pox5) are called HDC100. HDC100 is a non-revertible (pox4Δ::URA3/pox4Δ::URA3 pox5/pox5) strain. Since the transformed cells have all four POX 4 and POX 5 genes disrupted, they are β-oxidation blocked as there is little or no production of acyl-CoA oxidase, an enzyme required in the initial step of the β-oxidation pathway. The deletion of the portion of the POX 4 gene prevents further recombination to a POX 4 gene encoding a functional protein. Reversion to wild-type activity and reutilization of the dicarboxylic acid products through the β-oxidation pathway is therefore avoided. Accordingly, the resulting HDC100 strains produce little if any unwanted side products such as β-hydroxy acids, unsaturated acids, or shorter chain acids.

The resulting β-oxidation blocked C. tropicalis cell is a genetically modified C. tropicalis strain wherein a portion of one or more genes of the β-oxidation pathway has been deleted. Preferably, the deletion is to a portion of the chromosomal POX 4 or POX 5 genes, and in some embodiments other genes of the β-oxidation pathway have also been disrupted. While the process of the present invention may be used with a wild-type strain, it is especially suitable for use with strains in which the β-oxidation pathway is already blocked or partially blocked. The following strains may be transformed using the methods described herein: H53, in which both POX 5 genes are disrupted; H5343, in which all four POX 4 and POX 5 genes are disrupted; H41, in which the POX 4A gene is disrupted; H41B, in which the POX 4B gene is disrupted; H43, in which both POX 4 genes are disrupted; H435, in which one of the POX 5 genes and both POX 4 genes are disrupted; H51, in which one POX 5 gene is disrupted; H45, in which one POX 5 and the POX 4A genes are disrupted; H534, in which both copies of POX 5 and the POX 4A genes are disrupted; and H534B, in which both copies of POX 5 and the POX 4B genes are disrupted. Following the teachings of the present invention, any of the strains listed hereinabove may be transformed so that one or more alleles at the POX 4 or POX 5 locus is not only disrupted but also contains a deletion. The deleted portion of the POX 4 or POX 5 genes prevents the strain from reverting to wild-type activity.

In another embodiment, the C. tropicalis strain may also have one or more cytochrome P450 (P450ALK) genes and/or reductase (P450RED) genes amplified, which results in an increase in the amount of rate-limiting ω-hydroxylase through P450 gene amplification and an increase in the rate of substrate flow through the ω-oxidation pathway. In a preferred embodiment, CPR (reductase) genes, including the CPRA and CPRB genes of *C. tropicalis* 20336 as described in U.S. Pat. No. 6,331,420 and International Application No. PCT/US99/20797, are included.

Another aspect of the present invention involves using these transformed yeast strains to produce dicarboxylic acids. In a preferred embodiment, the substrate flow in transformed *C. tropicalis* strains is redirected to the ω-oxidation pathway as the result of functional inactivation of the competing β-oxidation pathway by POX gene disruption and deletion. Most preferred embodiments utilize the yeast strain HDC100, which is β-oxidation blocked and will not revert to wild-type activity as a result of a deletion of a portion of the POX 4 gene. These strains, when cultured on a suitable medium, demonstrate an increase in the specific production of substantially pure α,ω-dicarboxylic acids.

While suitable media conducive to the production of α,ω-dicarboxylic acids may readily be determined by those skilled in the art, in a most preferred embodiment the medium contains a nitrogen source, an organic substrate and a cosubstrate.

The nitrogen source of the culture medium may be any inorganic or organic source of nitrogen normally used in processes for culturing microorganisms. Inorganic nitrogen sources include alkali metal nitrates such as sodium or potassium nitrate, ammonium salts such as ammonium sulfate, ammonium chloride, ammonium nitrate, ammonium acetate, etc. Organic nitrogen sources include urea, corn steep liquor, yeast extracts, and other organic nitrogen sources known to those skilled in the art.

The organic substrate of the culture medium can be any aliphatic compound having from about 4 to about 22 carbon atoms wherein at least one of the terminal carbons is a methyl group, a terminal carboxyl group and/or a terminal functional group which is oxidizable to a carboxyl group by biooxidation. Such compounds include alkanes, alkenes, alkynes, carboxylic acids and their esters, and arenes. Preferred substrates are alkanes having from about 4 to about 22 carbon atoms and fatty acids and their methyl or ethyl esters wherein the acyl portion contains from about 4 to about 22 carbon atoms. The most preferred substrates are dodecane, tridecane, tetradecane, oleic acid, methyl oleate, methyl palmitate, methyl palmitoleate and methyl myristate.

The cosubstrate may include glucose, fructose, maltose, glycerol, sodium acetate and combinations thereof. The preferred cosubstrate is glucose. A cosubstrate is necessary because the β-oxidation pathway of *C. tropicalis* strains used in the methods of the invention are totally or partially blocked, and energy is not available from the oxidation of the substrate. Adding glucose at a defined rate along with the substrate strikes a balance between providing an energy source for the cells while allowing the partial oxidation of the substrate to an α,ω-dicarboxylic acid.

The following examples will serve to illustrate but not limit the invention.

EXAMPLES

A POX 4 disruption construct was designed to delete 653 bp of the POX 4 ORF while inserting a 1676 bp (647 bp promoter, 803 bp ORF and 226 bp UTR) URA 3 selectable marker gene. PCR primers were designed so as to amplify the two flanking regions (590 bp and 815 bp) of the POX 4 ORF. These primers included restriction sensitive cloning sites so as to facilitate cloning of the URA 3 gene. Upon successful PCR of the flanking POX 4 regions, the DNA was restricted, gel-isolated and used in a ligation to generate the desired POX 4 disruption construct. This construct was used to transform *C. tropicalis* H53 (pox5/pox5) ura- to a pox4/pox4 URA+ phenotype. *C. tropicalis* H53 was deposited on Sep. 26, 2007, with Deutsche Sammlung von Mikroorganismen Und Zellkulturen GmbH, Inhoffenstr. 7B, D-38124 Braunschweig, as Accession Number DSM 19687. Four *C. tropicalis* pox5/pox5 pox4/pox4 homozygotes were confirmed by Southern analysis. Moreover, these strains were unable to grow on dodecane/decane indicating their poxphenotype. These strains were labeled HDC100-1, -2, -3, and -4.

Example 1

Generation of POX 4 Flanking Sequences

In order to generate the POX 4 flanking sequences to direct integration of the disruption cassette, two sets of PCR primers were designed.

```
Set #1(5' to 3')
                                              (SEQ ID NO: 1)
218-27a-AGGCGCGCCCCATCCAAAAGGAAAGAGACAGC (SEQ ID NO: 2)
218-27b-CCTTAATTAACGTCAACAATCAATCTGGCGTAGAC

Set #2(5' to 3')
                                              (SEQ. ID NO. 3)
218-27c-CCTTAATTAATCACGGTTACTCGTCCTACAACGG (SEQ. ID NO. 4)
218-27d-AGCTTTGTTTAAACGCAGCGGTTTCATCAGACTTTTC
```

PCR fragments of these two flanking sequences were purified, restricted with AscI, PacI and PmeI restriction enzymes (AscI and PacI for the Set #1 fragment, and PacI and PmeI for the Set #2 fragment) and ligated to a gel purified, QiaexII cleaned AscI-PmeI digest of plasmid pNEB193 purchased from New England Biolabs (Beverly, Mass.). The ligation was performed with an equimolar number of DNA termini at 16° C. for 16 hours using T4 DNA ligase (New England Biolabs). Ligations were transformed into *E. coli* XL1-Blue cells (Stratagene, LaJolla, Calif.) according to manufacturers recommendations. White colonies were isolated, grown, plasmid DNA isolated and digested with AscI-PmeI to confirm insertion of the flanking sequences into pNEB193.

Restriction enzyme-sensitive cloning sites were incorporated into each primer as shown in italics. Primer set #1 was used to amplify a region of DNA from base pair 587-1177. Likewise, primer set #2 was used to amplify a region of DNA from base pair 1830-2645.

These fragments, when ligated to a nutritional marker (URA 3) produced in accordance with Example 2 below and upon integration into the *Candida tropicalis* genome, yielded a deletion of 653 base pairs of the POX 4 ORF from nucleotides 1178-1829 (see FIG. 1).

Example 2

Generation of a URA 3 Selectable Marker

A primer set was made to amplify a 1676 base pair URA 3 containing PacI restriction sensitive cloning sites.

```
(5' TO 3')
                                              (SEQ. ID. NO: 5)
Primer 179a-CCTTAATTAAGCTCACGAGTTTTGGGATTTTC (SEQ. ID. NO: 6)
Primer 179b-CCTTAATTAATGGATACCTTCAAGCAAGTG
```

Primers were designed and synthesized based on the 1712 bp sequence of the URA 3A gene of *C. tropicalis* 20336 (see FIG. 2). Primers 179a and 179b described above were used in PCR with *C. tropicalis* 20336 genomic DNA to amplify URA 3A sequences between nucleotides 9 and 1685 as shown in FIG. 2. These primers were also designed to introduce a unique PacI restriction site into the resulting amplified URA 3A fragment. PCR fragments of the URA 3A gene were purified, and restricted with PacI restriction enzymes. The resulting vector possessed a 1676 bp (647 bp promoter, 803 bp ORF and 226 bp UTR) URA 3 selectable marker gene with PacI restriction-sensitive cloning sites.

Example 3

Creation of a pox4-Deleted Disruption Construct

In order to make this disruption construct, the 1676 bp URA 3 selectable marker gene with PacI restriction-sensitive cloning sites produced in accordance with Example 2 was cloned into the PacI restricted and dephosphorylated pNEB193 vector containing the POX 4 flanking fragments produced in accordance with Example 1. In a preferred aspect of the present invention, no foreign DNA other than that specifically provided by synthetic restriction site sequences was incorporated into the DNA which was cloned into the genome of *C. tropicalis*, i.e., with the exception of restriction site DNA only native *C. tropicalis* DNA sequences were incorporated into the genome.

The PacI restricted pNEB193 vector containing the POX 4 flanking fragments produced in accordance with Example 1 was digested with PacI, Qiaex II cleaned, and dephosphorylated with Shrimp Alkaline Phosphatase (SAP) (United States Biochemical, Cleveland, Ohio) according to the manufacturer's recommendations. Approximately 500 ng of PacI linearized pNEB193 vector containing the POX 4 flanking fragments was dephosphorylated for 1 hour at 37° C. using SAP at a concentration of 0.2 Units of enzyme per 1 pmol of DNA termini. The reaction was stopped by heat inactivation at 65° C. for 20 minutes.

The PacI URA 3A fragment derived from the procedures described in Example 2 above was then ligated to the dephosphorylated pNEB193 vector containing the POX 4 flanking fragments which had also been digested with PacI. The ligation procedure followed the same steps described above in Example 1. The ligation mixture was transformed into *E. coli* XL1 Blue MRF' (Stratagene). Transformants were selected and screened for correct constructs containing the vector sequence, the POX 4 flanking sequences, the URA 3A selectable marker gene, and missing the region between the POX 4 flanking sequences (653 base pairs of the POX 4 ORF from nucleotides 1178-1829 (see FIG. 1)). The constructs identified as being correct were sequenced and compared to the URA 3A sequence to confirm that PCR did not introduce DNA base changes that would result in an amino acid change.

Example 4

Transformation of *C. tropicalis* Using Lithium Acetate

Following ligation and confirmation of the construct described above in Example 3, AscI and PmeI liberated a 3083 base pair fragment which was used to transform, by a lithium acetate transformation protocol, a *Candida tropicalis* strain (H53) in which the POX 5 gene had previously been disrupted to uracil prototrophy.

The lithium acetate transformation protocol used to transform the *C. tropicalis* was in accordance with the general procedures described in Current Protocols in Molecular Biology, Supplement 5, 13.7.1 (1989), incorporated herein by reference. 5 ml of YEPD was inoculated with *C. tropicalis* H53 (previously disrupted to uracil prototrophy) from a frozen stock and incubated overnight on a New Brunswick shaker at 30° C. and 170 rpm. The next day, 10 μl of the overnight culture was inoculated into 50 ml YEPD and growth was continued at 30° C., 170 rpm. The following day the cells were harvested at an $OD_{600}$ of 1.0. The culture was transferred to a 50 ml polypropylene tube and centrifuged at 1000×g for 10 min. The cell pellet was resuspended in 10 ml sterile TE (10 mM Tris-CI and 1 mM EDTA, pH 8.0). The cells were again centrifuged at 1000×g for 10 min and the cell pellet was resuspended in 10 ml of a sterile lithium acetate solution [LiAc (0.1 M lithium acetate, 10 mM Tris-CI, pH 8.0, 1 mM EDTA)]. Following centrifugation at 1000×g for 10 min., the pellet was resuspended in 0.5 ml LiAc. This solution was incubated for one hour at 30° C. while shaking gently at 50 rpm. A 0.1 ml aliquot of this suspension was incubated with 5 μg of transforming DNA at 30° C. with no shaking for 30 min. A 0.7 ml PEG solution (40% wt/vol polyethylene glycol 3340, 0.1 M lithium acetate, 10 mM Tris-CI, pH 8.0, 1 mM EDTA) was added and incubated at 30° C. for 45 min. The tubes were then placed at 42° C. for 5 min. A 0.2 ml aliquot was plated on synthetic complete media minus uracil (SC-uracil) (Kaiser et al. Methods in Yeast Genetics, Cold "Spring Harbor Laboratory Press, USA, 1994, incorporated herein by reference). Growth of transformants was monitored for 5 days. After three days, several transformants were picked and transferred to SC-uracil plates for genomic DNA preparation and screening. The transformants were identified as strain HDC100. HDC100 was deposited at the Deutsche Sammlung von Microorganismen Und Zellkulturen GmbH (DSMZ), Inhoffenstr. 7B, D-38124, Braunschweig, under Accession No. DSM19688 on Sep. 19, 2007, and converted to a deposit under the Budapest Treaty at DSM under Accession No. DSM19688 on Mar. 4, 2014.

Example 5

Transformant Analysis

The transformants prepared in accordance with Example 4 were then analyzed. Transformants were initially plated onto media containing dodecane and decane as the sole carbon sources. Transformants that failed to grow or grew slowly on this media (indicating that one or both of the POX 4 genes were disrupted) while retaining uracil prototrophy were subjected to Southern analysis. Intensity of the band signal from the Southern analysis was used as a measure of the integration events (i.e. the more copies of the URA 3A selectable marker gene which are present, the stronger the hybridization signal).

Transformants were grown at 30° C., 170 rpm, in 10 ml SC-uracil media for preparation of genomic DNA. Following the isolation of genomic DNA from the transformants, the DNA was digested with PacI or EcoRI and the digests were processed according to the standard Southern method. A 0.95% agarose gel was used to prepare a Southern hybridization blot. The DNA from the gel was transferred to a Magna-Charge nylon filter membrane (MSI Technologies, Westboro, Mass.) according to the alkaline transfer method of Sambrook et al, Molecular Cloning: A Laboratory Manual, 2ed. Cold Spring Harbor Press, USA (1989). For the Southern hybridization, a 1.7 kb URA 3 DNA fragment was used as a hybridization probe of the PacI digests and a 6.6 Kb POX 4 probe was used for the EcoRI digests. 300 ng of URA 3A DNA was labeled using a ECL Direct labeling and detection system (Amersham) and the Southerns were processed according to the ECL kit specifications. The blot was processed in a volume of 30 ml of hybridization fluid corresponding to 0.125 ml/cm². Following a prehybridization at 42° C. for 1 hour, 300 ng of URA 3A probe was added and the hybridization continued for 16 hours at 42° C. Following hybridization, the blots were washed two times for 20 minutes each at 42° C. in primary wash containing urea. Two 5 minute secondary washes at RT were conducted, followed by detection according to directions. The blots were exposed for 16 hours as recommended.

Only those strains receiving the disruption/deletion construct yielded the anticipated 1.676 Kb band. The presence of an 11.8 Kb fragment indicated that the POX 4 gene was disrupted. The presence of a 10.8 Kb fragment indicated that the POX 4 gene was wild-type. In those cases where both a wild-type allele and a disrupted allele were present, those strains were subjected to 5-fluoroorotic acid (5-FOA) treatment to regenerate the URA 3 selectable marker.

Strains were tested for growth in media containing various concentrations of 5-FOA, an analogue of a uracil pathway intermediate which is toxic to Ura+ cells. Both strains were grown to mid-log phase in YEPD medium (2% Bacto-peptone, 2% glucose, 1% Bacto-Yeast Extract) and were plated at various dilutions onto FOA medium (Boeke et al., [1984] Molec. Gen. Genet. 197; p 345-346) or YEPD medium.

Strains that were identified as uracil auxotrophs were transformed again with the disruption construct so as to disrupt the non-disrupted POX 4 allele. The presence of a single 11.8 Kb band indicated the disruption of both alleles of the POX 4 gene. Four *C. tropicalis* pox5/pox5 pox4/pox4 homozygotes were confirmed by Southern analysis. These strains were HDC100-1, -2, -3, and -4.

Example 6

Fermentation Analysis of Non-Reversion

Under fermentation conditions using strain H5343 or its progeny, reversion to O-oxidation typically occurred around 72 hours post substrate induction. This condition can be facilitated by glucose limitation. When the same conditions of fermentation that induce β-oxidation in H5343 were applied to HDC100, no reversion to β-oxidation was observed. This indicated that β-oxidation was still disrupted in HDC100. Moreover, when samples of these fermentation cultures were plated onto media containing dodecane and decane as the sole carbon sources, no growth of HDC100 was observed, indicating their pox-phenotype.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A *Candida tropicalis* cell derived from *Candida tropicalis* strain H53 by deletion of a 653 base pair portion of a coding region of a POX 4 gene open reading frame of strain H53 and insertion of a 1676 base pair URA 3 marker gene in the POX 4 coding region, wherein the cell is a cell of strain HDC100.

2. A process for producing a substantially pure α,ω-dicarboxylic acid which comprises culturing the *Candida tropicalis* cell of claim 1 in a culture medium containing a nitrogen source, an organic substrate and a cosubstrate.

3. A *Candida tropicalis* cell of strain HDC100.

4. A process for producing a substantially pure α,ω-dicarboxylic acid which comprises culturing the *Candida tropicalis* cell of claim 3 in a culture medium containing a nitrogen source, an organic substrate and a cosubstrate.

5. A *Candida tropicalis* cell of strain HDC100 deposited under Accession No. DSM19688.

6. A process for producing a substantially pure α,ω-dicarboxylic acid which comprises culturing the *Candida tropicalis* cell of claim 5 in a culture medium containing a nitrogen source, an organic substrate and a cosubstrate.

* * * * *